United States Patent
Meinhardt et al.

(10) Patent No.: US 6,532,769 B1
(45) Date of Patent: Mar. 18, 2003

(54) GLASS-CERAMIC JOINT AND METHOD OF JOINING

(75) Inventors: Kerry D. Meinhardt, Richland, WA (US); John D. Vienna, West Richland, WA (US); Timothy R. Armstrong, Clinton, TN (US); Larry R. Pederson, Kennewick, WA (US)

(73) Assignee: Battelle Memorial Institute, Richland, WA (US)

( * ) Notice: Subject to any disclaimer, the term of this patent is extended or adjusted under 35 U.S.C. 154(b) by 0 days.

(21) Appl. No.: 09/562,583

(22) Filed: May 1, 2000

Related U.S. Application Data

(63) Continuation-in-part of application No. 09/365,343, filed on Jul. 30, 1999, now Pat. No. 6,430,966.

(51) Int. Cl.$^7$ .............................................. C03C 10/08
(52) U.S. Cl. ........................... 65/33.5; 65/33.6; 65/36; 65/43; 501/15; 501/16
(58) Field of Search ................................. 65/33.5, 33.6, 65/36, 43; 501/14, 15, 16, 21, 23, 24

(56) References Cited

U.S. PATENT DOCUMENTS

| | | | |
|---|---|---|---|
| 4,291,107 A | 9/1981 | Barry et al. | 429/104 |
| 5,273,837 A | * 12/1993 | Aitken et al. | 429/30 |
| 5,479,700 A | * 1/1996 | Nachlas et al. | 29/825 |

FOREIGN PATENT DOCUMENTS

| | | |
|---|---|---|
| DE | 3134739 | 4/1982 |
| EP | 055 049 | 6/1982 |
| EP | 220 813 | 5/1987 |
| EP | 351 097 | 1/1990 |
| GB | 1019821 | 3/1963 |
| JP | 59-219850 | 11/1984 |

OTHER PUBLICATIONS

Y Sakaki et al., "Glass–Ceramics Sealants in $CaO-Al_2-SiO_2$ System", p. 652–660.1997. (no month available).

C Günther et al., "The Stability of the Sealing Glass AF 45 In $H_2/H_2O$—and $O_2/N_2$—Atmospheres", p. 746–756. 1997 (no month available).

KL Ley et al., "Glass–Ceramic Sealants for Solid Oxide Fuel Cells: Part. 1 Physical Properties", p. 1489–1493. Jan. 1996.

PH Larsen et al., "Stacking of Planar SOFCs", p. 69–77. 1995. (no month available).

* cited by examiner

Primary Examiner—Sean Vincent
(74) Attorney, Agent, or Firm—Stephen R. May

(57) ABSTRACT

The present invention is a glass-ceramic material and method of making useful for joining a solid ceramic component and at least one other solid component. The material is a blend of M1-M2-M3, wherein M1 is BaO, SrO, CaO, MgO, or combinations thereof, M2 is $Al_2O_3$, present in the blend in an amount from 2 to 15 mol %, M3 is $SiO_2$ with up to 50 mol % $B_2O_3$ that substantially matches a coefficient of thermal expansion of the solid electrolyte. According to the present invention, a series of glass ceramics in the M1-$Al_2O_3$-M3 system can be used to join or seal both tubular and planar solid oxide fuel cells, oxygen electrolyzers, and membrane reactors for the production of syngas, commodity chemicals and other products.

19 Claims, 2 Drawing Sheets

M1 = BaO + CaO + SrO + MgO
M3 = $B_2O_3$ + $SiO_2$

M1 = BaO + CaO + SrO + MgO
M3 = B$_2$O$_3$ + SiO$_2$

GLASS-CERAMIC JOINT AND METHOD OF JOINING

This application is a continuation-in-part of application Ser. No. 09/365,343 filed Jul. 30, 1999 now U.S. Pat. No. 6,430,966.

This invention was made with Government support under Contract DE-AC0676RLO1830 awarded by the U.S. Department of Energy. The Government has certain rights in the invention.

FIELD OF THE INVENTION

The present invention is a glass ceramic material and method of making, specifically for use in electrochemical devices such as fuel cells, gas sensors, oxygen or hydrogen pumps/separators, or for sealing any material with a thermal expansion coefficient similar to the seal material.

As used herein, the terms "solid electrolyte" or "solid oxide ion conducting electrolyte" are interchangeable.

As used herein, the term "joint" includes the term "seal" because, in this glass-ceramic field, the "seal" joins at least two parts. However, the "joint" may be intermittent thereby not serving as a "seal".

BACKGROUND OF THE INVENTION

Ceramic materials are being used more often from automobile turbochargers to experimental fuel cells. However, there remains the problem of joining and/or sealing ceramic components to other ceramic components, to metal components, or to combinations thereof (e.g., cermet components) such that the joint maintains integrity during operation. For example, solid oxide ion conducting electrolytes are useful for oxygen separation and high temperature fuel cells. Although many technical challenges of their development have been overcome, there remains the problem of sealing. In a planar design, a gas-tight seal must bond the components together and prevent the mixing of the gas species on both sides of the solid oxide ion conducting electrolyte.

A limited number of materials are suitable as a solid oxide ion conducting electrolyte. The most commonly used materials are yttria stabilized zirconia (YSZ), doped ceria, doped bismuth oxide and doped lanthanum gallate. The thermal expansion coefficient of these materials can range from $10.1 \times 10^{-6}$ to $14.3 \times 10^{-6\circ}$ $C.^{-1}$ depending on the type of dopant and concentration. The operating temperature can also range from 700° C. to 1000° C. depending upon which material is chosen as the electrolyte. Therefore, the seal material must be tailored to match the electrolyte thermal expansion, maintain a gas tight seal at temperatures ranging from 200° C. to 1200° C., and not have detrimental chemical interactions with the fuel cell components. In addition, the seal material must also be stable at the operating temperature (800–1000° C.) for extended periods of time (>9,000 hr) and be electrically insulating. For a solid oxide fuel cell, the seal must be able to survive extremely reducing environments.

Various efforts to seal solid oxide ion conducting devices have been made with varying degrees of success. Silica, boron, and phosphate-based glasses and glass-ceramics have been evaluated as a sealing material[1-4] for solid oxide fuel cells. Experiments conducted by P. H. Larsen et all have shown major problems with glasses purely based on phosphate as the glass former. At temperature, the phosphate volatilized and reacted with the anode to form nickel phosphide and zirconiumoxyphosphate. Additionally, these phosphate glasses usually crystallized to form meta- or pyrophosphates, which exhibited low stability in a humidified fuel gas at the operating temperature.

Borosilicate glasses and glass ceramics have also been considered as potential seal materials. These glasses have been investigated by C. Günther et al[2] and K. L. Ley et al[3] for use in solid oxide fuel cells. However, boron will react with a humidified hydrogen atmosphere to form the gaseous species $B_2(OH)_2$ and $B_2(OH)_3$ at the operating temperature[2]. Therefore, any high boron seal may corrode in a humidified hydrogen environment over time. Glasses with $B_2O_3$ as the only glass former have showed up to a 20% weight loss in the humidified hydrogen environment and extensive interactions with fuel cell component materials both in air and wet fuel gas.[1]

Silica-based glasses and glass-ceramics offer the most promise. They typically have a higher chemical resistance and show minimal interaction with the fuel cell component materials. Unfortunately, these glasses tend to have thermal expansions below the range needed for a sealing material.

At the operating temperature, most glasses will crystallize with time. Therefore, it is critical to have a glass composition in which the thermal expansion coefficient after crystallization is compatible with the solid oxide ion conducting electrolyte. Once the glass is fully crystallized, it is typically very stable over time. In addition, crystallized glasses tend to be stronger mechanically at operating temperature, improving seal performance.

Hence, there is a need in the art for a sealing material that can operate at an operating temperature up to about 900° C., has a thermal expansion coefficient between $8 \times 10^{-6}$ and $15 \times 10^{-6\circ}$ $C.^{-1}$, and has no detrimental chemical interactions with the components.

BACKGROUND BIBLIOGRAPHY

1. P. H. Larsen, C. Bagger, M. Mogensen and J. G. Larsen, Proc. $4^{th}$ Int. Symp. Solid Oxide Fuel Cells, Volume 95-1, 1995, pp. 69–78.
2. C. Gunther, G. Hofer and W. Kleinlein, Proc. $5^{th}$ Int. Symp. Solid Oxide Fuel Cells, Volume 97-18, 1997, pp. 746–756.
3. K. L. Ley, M. Krumpelt, R. Kumar, J. H. Meiser, and I. Bloom, J. Mat. Res., Vol. 11, No. 6, (1996) pp. 1489–1493.
4. Yoshinori Sakaki, Masatoshi Hattori, Yoshimi Esaki, Satoshi Ohara, Takehisa Fukui, Kaseki Kodera, Yukio Kubo, Proc. $5^{th}$ Int. Symp. Solid Oxide Fuel Cells, Volume 97-18, 1997, pp. 652–660.

SUMMARY OF THE INVENTION

The present invention is a glass-ceramic compound and method of making that are useful in joining or sealing ceramic components to other ceramic components, to metal components, or to combinations thereof (e.g., cermet components). More specifically, the present invention is useful for joining/sealing in an electrochemical cell having at least one solid electrolyte having a first and second side exposed to first and second gas species respectively. The seal is necessary for separating the first and second gas species.

The glass-ceramic compound contains at least three metal oxides, M1-M2-M3. M1 is BaO, SrO, CaO, MgO, or combinations thereof. M2 is $Al_2O_3$ and is present in the compound in an amount from 2 to 15 mol %. M3 is $SiO_2$ with up to 50 mol % $B_2O_3$. The compound substantially matches a coefficient of thermal expansion of the solid ceramic component and at least one other solid component that is either ceramic, metal, or a combination thereof.

According to the present invention, a series of glass ceramics in the M1-Al$_2$O$_3$-M3 system can be used to join or seal both tubular and planar ceramic solid oxide fuel cells, oxygen electrolyzers, and membrane reactors for the production of syngas, commodity chemicals and other products.

It is an object of the present invention to provide a compound useful for joining or sealing a solid electrolyte or a solid oxide ion conducting electrolyte.

An advantage of a joint/seal made with the compound of M1-Al$_2$O$_3$-M3 is the maintaining of a substantially constant coefficient of thermal expansion from the glass to crystalline phase.

The subject matter of the present invention is particularly pointed out and distinctly claimed in the concluding portion of this specification. However, both the organization and method of operation, together with further advantages and objects thereof, may best be understood by reference to the following description taken in connection with accompanying drawings wherein like reference characters refer to like elements.

DESCRIPTION OF THE PREFERRED EMBODIMENT(S)

The present invention is a glass-ceramic compound and method of making the glass-ceramic compound. The present invention is useful for joining or sealing between at least two solid ceramic parts, for example a seal in an electrochemical cell having at least one solid electrolyte having a first and second side exposed to first and second gas species respectively. The present invention is also useful for joining or sealing between a solid ceramic component and a metal component or a cermet component. The seal is necessary for separating the first and second gas species during operation, usually at elevated temperatures.

The present invention includes a joint between a solid ceramic component and at least one other solid component that is preferably a solid ceramic component, a metal component, or a combination thereof such as a cermet component. The joint has at least three metal oxides of M1-M2-M3. M1 is BaO, SrO, CaO, MgO, or combinations thereof. M2 is Al$_2$O$_3$. M3 is SiO$_2$ with up to 50 mol % B$_2$O$_3$. The joint substantially matches a coefficient of thermal expansion of the components comprising the joint. The coefficient of thermal expansion of the joint is from about $7 \times 10^{-6}$ °C.$^{-1}$ to about $15 \times 10^{-6}$ °C.$^{-1}$ as measured from 25° C. to 1000° C.

Figure 1:
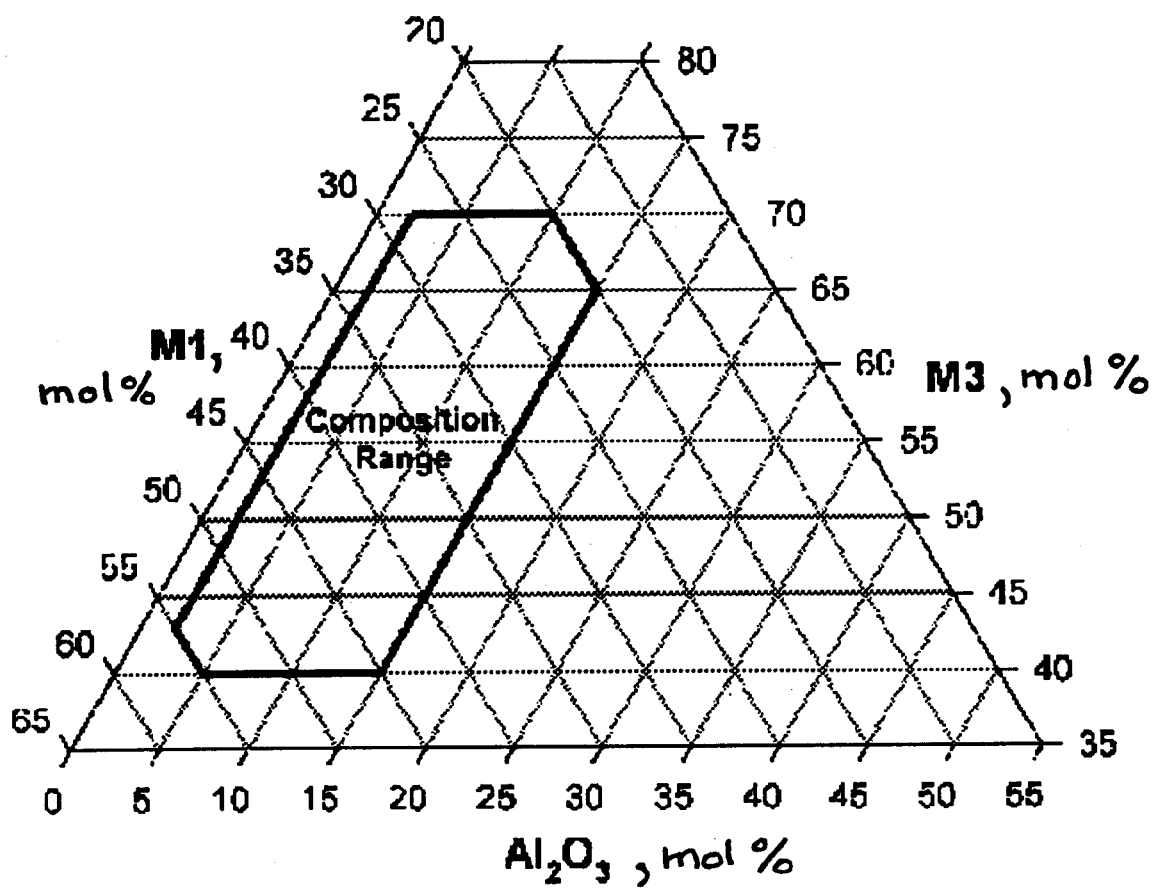
FIG. 1 is a phase diagram showing the compositional range of the M1-Al$_2$O$_3$-M3 joint/seal material according to the present invention.

The composition of the joint/seal is preferably in the range wherein M1 is present in an amount from about 20 mol % to about 55 mol %, Al$_2$O$_3$ is present in an amount from about 2 mol % to about 15 mol %, and M3 is present in an amount from about 40 mol % to about 70 mol %. The compositional range for the M1-Al$_2$O$_3$-M3 system is shown in FIG. 1.

The glass-ceramic compound may further contain at least one additional metal oxide including, but not limited to, ZrO$_2$, TiO$_2$, Cr$_2$O$_3$, and combinations thereof to modify the properties of the glass phase or the final crystallized seal. Properties include, but are not limited to, wetting, glass transition temperature (Tg), glass softening temperature (Ts), thermal expansion coefficient, and combinations thereof.

The range of thermal expansion coefficients for both glass-ceramic and crystallized glass-ceramic is from $7 \times 10^{-6}$ to $13 \times 10^{-6}$ °C.$^{-1}$. The glass transition temperatures (Tg) and softening temperature (Ts) for the glass-ceramics are in the range of 650°–800° C. However, the crystallized glass-ceramic has a softening temperature above 1000° C.

Substantially the same coefficient of thermal expansion is herein defined as the coefficient of thermal expansion of the seal material within about 30%, preferably within about 16%, more preferably within about 5% of the sealed material.

The joint may be used in an electrochemical test cell to join an oxygen ion pump and a test material. In addition, the joint may be used in an oxygen generator or a fuel cell to join an oxygen ion conducting electrolyte, for example a zirconia electrolyte, and an interconnect, for example manganite, chromite, metal, and combinations thereof.

According to the present invention, a method of joining a solid ceramic component with at least one other solid component has the steps of:

(a) providing a blend of M1, Al$_2$O$_3$, and M3 that substantially matches a coefficient of thermal expansion of a solid ceramic component and at least one other solid component, which is preferably another ceramic component, a metal component, or a combination thereof such as a cermet component. M1 is BaO, SrO, CaO, MgO, or combinations thereof. Al$_2$O$_3$ is present in the blend in an amount from 2 to 15 mol %. M3 is SiO$_2$ with up to 50 mol % B$_2$O$_3$;

(b) placing said blend at an interface of said solid ceramic component and said at least one other solid component as a pre-assembly;

(c) heating said pre-assembly to a temperature sufficient to cause the blend to flow into and wet the interface as an assembly; and (d) cooling said assembly and solidifying said blend thereby joining said solid ceramic component and said at least one other solid component.

EXAMPLE 1

An experiment was conducted to demonstrate the glass-ceramic materials (referred to simply as "glass" in Tables E1-1 and E1-2 and FIG. 2) of the present invention.

Table E1-1 shows several compositions. The major crystallized phases include BaO·2SiO$_2$, 2BaO·3SiO$_2$, BaO·SiO$_2$, and BaO·Al$_2$O$_3$·2SiO$_2$.

TABLE E1-1

| | Glass-Ceramic Material Compositions | | | | | |
|---|---|---|---|---|---|---|
| Glass | Glass Composition (mole %) | | | | | |
| ID # | BaO | SrO | CaO | Al$_2$O$_3$ | B$_2$O$_3$ | SiO$_2$ |
| 1 | 34.8 | 4.8 | — | 10.4 | — | 50.0 |
| 3 | 33.0 | 5.0 | — | 7.7 | — | 54.3 |
| 7b | 33.7 | — | — | 10.5 | — | 55.8 |
| 9 | 36.9 | — | — | 10.5 | — | 52.6 |
| 10 | 42.5 | — | — | 7.5 | — | 50.0 |
| 11 | 45.0 | — | — | 5.0 | — | 50.0 |
| 12 | 41.3 | — | — | 5.0 | — | 53.7 |

TABLE E1-1-continued

Glass-Ceramic Material Compositions

| Glass ID # | Glass Composition (mole %) | | | | | |
|---|---|---|---|---|---|---|
| | BaO | SrO | CaO | $Al_2O_3$ | $B_2O_3$ | $SiO_2$ |
| 13 | 37.5 | — | — | 5.0 | — | 57.5 |
| 1d | 34.8 | — | 4.8 | 10.4 | — | 50.0 |
| 14 | 30.0 | — | 10.0 | 10.0 | 20.0 | 30.0 |
| 15 | 25 | | 10 | 15 | 15 | 35 |
| 17 | 20 | | 10 | 5 | 30 | 35 |
| 18 | 35 | | 15 | 5 | 10 | 35 |

Figure 2:
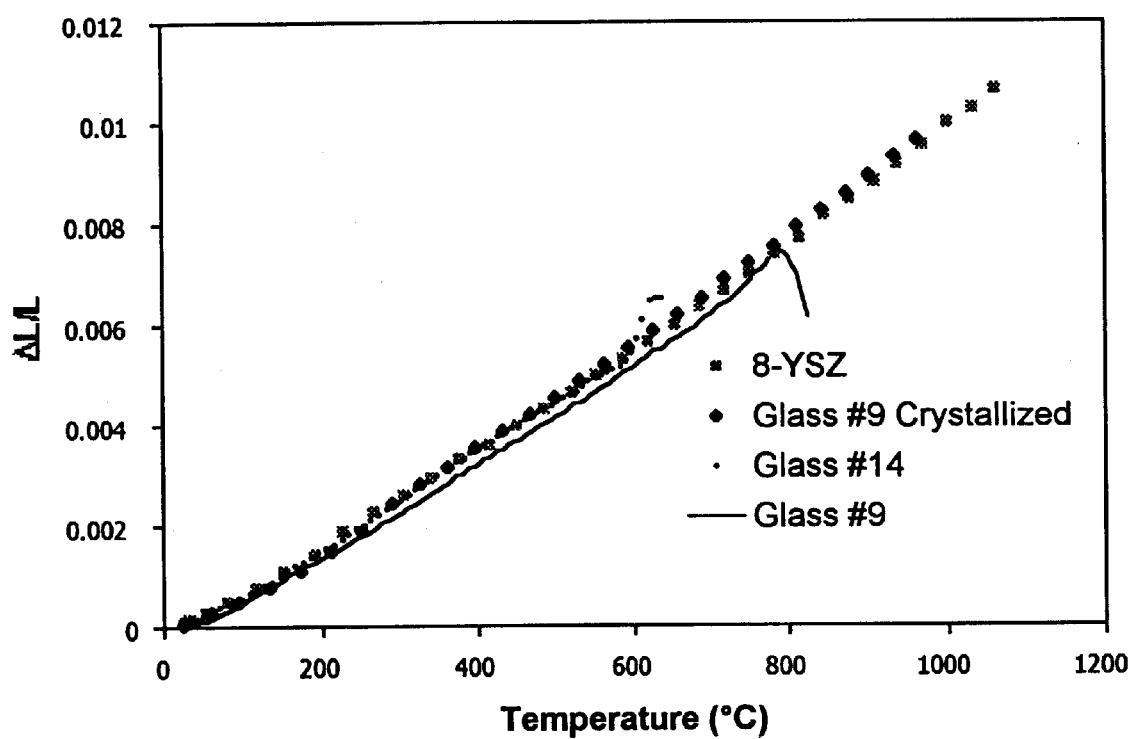
FIG. 2 is a graph of coefficient of thermal expansion versus temperature for a solid electrolyte and the glass-ceramic material of the present invention.

FIG. 2 illustrates how well the glass-ceramic material was tailored to match a solid electrolyte. The solid electrolyte material was 8-YSZ and the glass-ceramic compositions were #9 and #14 (i.e., Glass IDs #9 and #14). The thermal expansion of the crystallized glass-ceramic materials was within 0.06% of the expansion of the solid electrolyte material.

Table E1-2 shows properties of the glass-ceramic material of the present invention.

TABLE E1-2

Glass-Ceramic Material Properties

| Glass ID # | Glass Transition Temperature (Tg, ° C.) | Softening Temperature (Ts, ° C.) | Thermal Expansion (Glass, 25° C. to Tg) | Thermal Expansion (Crystallized Glass, 25° C. to 1000° C.) |
|---|---|---|---|---|
| 1 | 700 | 760 | 10.3 | 12.8 |
| 3 | 728 | 791 | 9.5 | 9.2 |
| 7b | 760 | 803 | 8.8 | 7.6 |
| 9 | 726 | 803 | 9.4 | 10.5 |
| 10 | 736 | 788 | 11.2 | 13.4 |
| 11 | 710 | 763 | 11.4 | 14.6 |
| 12 | 702 | 749 | 11.5 | 12.8 |
| 13 | 695 | 745 | 11.1 | 9.6 |
| 1d | 738 | 802 | 10.0 | 11.5 |
| 1e | 720 | 783 | 10.4 | 12.5 |
| 14 | 597 | 640 | 9.48 | — |
| 15 | 620 | 684 | 7.5 | — |
| 17 | 621 | 670 | 7.85 | — |
| 18 | 588 | 650 | 10.8 | — |

EXAMPLE 2

Seals formed from a glass frit were used to fabricate sealed 8YSZ oxygen pumps. A zirconia pump of fully dense small closed end tube and test material of flat plate of 8 mol % stabilized zirconia were sealed together with a mixture of 70 wt % glass-ceramic composition #9 and 30 wt % glass-ceramic composition #14 to assemble an electrochemical test cell. The tube was electroded with Pt on both the inside and outside to function as an oxygen pump. Pt leads were connected to the electrodes. The pre-assembly was placed in a furnace, heated to 1150° C. to seal. The temperature was reduced after sealing to the crystallization temperature and held there until the seal crystallized. After crystallization, the assembly was allowed to cool to room temperature The assembly was tested by pumping oxygen out of the sealed assembly and found capable of reaching a partial pressure of oxygen of $1 \times 10^{-18}$ atm at 1000° C. An oxygen leak rate of $3.7 \times 10^{-5}$ standard cubic centimeters per sec (sccs) was calculated from the pumping current. This is adequate for solid oxide fuel cells and oxygen generators.

CLOSURE

While a preferred embodiment of the present invention has been shown and described, it will be apparent to those skilled in the art that many changes and modifications may be made without departing from the invention in its broader aspects. The appended claims are therefore intended to cover all such changes and modifications as fall within the true spirit and scope of the invention.

We claim:

1. A joint between a solid ceramic component and at least one other solid component, said joint comprising: at least three metal oxides of M1-M2-M3 wherein M1 is selected from the group consisting of BaO, SrO, CaO, MgO, and combinations thereof and wherein M1 is present in an amount from about 20 mol % to about 55 mol % and MgO is less than 90 mol % of that group and SrO is less than 24 mol % of the total, M2 is $Al_2O_3$ and wherein M2 is present in an amount from 2 to 15 mol %, and M3 is $SiO_2$ with at least some $B_2O_3$ and up to 50 mol % of $B_2O_3$ and wherein M3 is present in an amount from about 40 mol % to about 70 mol %, said joint substantially matching a coefficient of thermal expansion of said solid ceramic component and said at least one other solid component.

2. The joint as recited in claim 1, wherein said at least one other solid component is ceramic.

3. The joint as recited in claim 1, wherein said at least one other solid component is metal.

4. The joint as recited in claim 1, wherein said at least one other solid component is cermet.

5. The joint as recited in claim 1 that is a seal.

6. The joint as recited in claim 1 wherein said coefficient of thermal expansion is from about $7 \times 10^{-6}$ °$C.^{-1}$ to about $15 \times 10^{-6}$ °$C.^{-1}$ as measured from 25° C. to 1000° C.

7. The joint as recited in claim 1, further comprising at least one additional metal oxide.

8. The joint as recited in claim 7, wherein said at least one additional metal oxide is selected from the group consisting of $ZrO_2$, $TiO_2$, $Cr_2O_3$, and combinations thereof.

9. The joint as recited in claim 1, wherein said solid ceramic component and said at least one other solid component are an oxygen ion pump and a test material in an electrochemical test cell.

10. The joint as recited in claim 1, wherein said solid ceramic component and said at least one other solid component are an oxygen ion conductor and an interconnect in an oxygen generator.

11. The joint as recited in claim 1, wherein said solid ceramic component and said at least one other solid component are an oxygen ion conductor and an interconnect in a fuel cell.

12. A method of joining a solid ceramic component and at least one other solid component, comprising the steps of:

(a) providing a blend of M1-M2-M3 wherein M1 is selected from the group consisting of BaO, SrO, CaO, MgO, and combinations thereof and wherein M1 is present in an amount from about 20 mol % to about 55 mol % and MgO is less than 90 mol % of that group and SrO is less than 24 mol % of the total, M2 is $Al_2O_3$ and wherein M2 is present in an amount from 2 to 15 mol %, and M3 is $SiO_2$ with at least some $B_2O_3$ and up to 50 mol % of $B_2O_3$ and wherein M3 is present in an amount from about 40 mol % to about 70 mol %, that substantially matches a coefficient of thermal expansion of said solid ceramic component and said at least one other solid component;

(b) placing said blend at an interface of said solid ceramic component and said at least one other solid component as a pre-assembly;

(c) heating said pre-assembly to a temperature sufficient to cause the blend to flow into said interface as an assembly; and (d) cooling said assembly and solidifying said blend thereby joining said solid ceramic component and said at least one other solid component.

13. The method as recited in claim 12, wherein said joining is sealing.

14. The method as recited in claim 12, wherein said coefficient of thermal expansion is from about $7\times10^{-6}$ $C.^{-1}$ to about $15\times10^{-6}$ $C.^{-1}$ as measured from 25° C. to 1000° C.

15. The method as recited in claim 12, further comprising at least one additional metal oxide.

16. The method as recited in claim 15, wherein said at least one additional metal oxide is selected from the group consisting of $ZrO_2$, $TiO_2$, $Cr_2O_3$, and combinations thereof.

17. The method as recited in claim 12, wherein said solid ceramic component and said at least one other solid component are an oxygen ion pump and a test material in an electrochemical test cell.

18. The method as recited in claim 12, wherein said solid ceramic component and said at least one other solid component are an oxygen ion conductor and an interconnect in a fuel cell.

19. The joint as recited in claim 12, wherein said solid ceramic component and said at least one other solid component are an oxygen ion conductor and an interconnect in an oxygen generator.

* * * * *